United States Patent [19]

Tosti

[11] Patent Number: 4,981,681
[45] Date of Patent: Jan. 1, 1991

[54] LOTION MIXTURE AND METHOD OF TREATING PSORIASIS

[76] Inventor: Vittorio Tosti, Eagle Pharmaceuticals, 345F Central Ave., Bohemia, N.Y. 11716

[21] Appl. No.: 237,280

[22] Filed: Aug. 26, 1988

[51] Int. Cl.$^5$ ...................... A61K 31/685; A61K 7/48
[52] U.S. Cl. ........................................ 424/78; 514/159; 514/356; 514/560; 514/458; 514/848; 514/863
[58] Field of Search ............... 424/195.1, 69; 514/159, 514/356, 560, 78, 458, 848, 52, 863

[56] References Cited

U.S. PATENT DOCUMENTS

| | | | |
|---|---|---|---|
| 4,021,573 | 5/1977 | Lee | 514/560 |
| 4,190,669 | 2/1980 | Voorhees | 514/529 |
| 4,325,965 | 4/1982 | Chiba | 514/458 |
| 4,518,614 | 5/1985 | Parkinson | 511/2 |
| 4,608,370 | 8/1986 | Aronsohn | 514/159 |
| 4,783,450 | 11/1988 | Fawzi et al. | 514/78 |

FOREIGN PATENT DOCUMENTS 2514873 10/1976 Fed. Rep. of Germany .

OTHER PUBLICATIONS

Hawley, "The Condensed Chemical Dictionary", 9th ed. Von Nostrand Reinhold, pp. 178, 183, 382, 417 and 456.

*Primary Examiner*—John W. Rollins, Jr.
*Attorney, Agent, or Firm*—Richard L. Miller

[57] ABSTRACT

A combination of ingredients consisting of a mixture of predetermined proportions of Purified Water, Methylparaben, Potassium Hydroxide, Hydrogenated Coconut Oil, Glycerine, Polysorbate 60, Polysorbate 80, Glyceryl Stearate (and) Laureth-23, White Wax, Stearic Acid, Cetyl Alcohol, PEG-40 Stearate, Glyceryl Stearate, Salicylic Acid, HQ Squalane, DL-Alpha Tocopherol Nicotinate, Isopropyl Myristate, EPA, Lecithin, Niacin, Vitamin B6, and Propylparaben, and said aforementioned ingredients having been found to constitute a safe method of treating psoriasis, consisting of the daily application on a person's skin on a daily bases of predetermined dosages of said ingredients.

2 Claims, No Drawings

LOTION MIXTURE AND METHOD OF TREATING PSORIASIS

FIELD OF INVENTION

The present invention relates to a method for treating psoriasis and more particularly it relates to a method of treating psoriasis by systematic and periodic application of several selected ingredients including the active ingredient Salicylic Acid.

BACKGROUND OF INVENTION

A great number of people suffer from the chronic anguish of psoriasis. Irregularly shaped and slightly raised dull red blotches appear on the sufferer's skin. These characteristic patches of psoriasis are covered by grayish or silvery scales which, if scratched, will peel and flake off like dandruff The lesions of psoriasis, which in the early stages can be misdiagnosed as ringworm, may appear anywhere on the body, although psoriasis does afflict certain parts of the body more than others, such as the scalp (psoriasis of the scalp is often mistaken for dandruff), elbows, knees and the trunk of the body.

The medical profession ascribes no definite cause to this embarrassing and unsightly disease, and no effective treatment has been offered. This vexatious scaling disease forces its sufferers to try everything in the dermatologist's chemical arsenal—tar, mercury, chrysarobin and phenol. These may bring some measure of transient relief, but recurrent outbreaks are the necessary outcome. In some instances, dermatologists even resort to X-ray therapy, which carries the obvious risk of dangerous side effects.

Unfortunately, one of the medications in current use that brings the most relief, also exacts the highest price in side effects; it is methotrexate, a highly toxic, anticancer drug which is known to cause severe liver damage. Conceived for the treatment of leukemia, this drug, an antimetabolite, has been used against psoriasis. While the drug is recommended only for severe, recalcitrant cases of psoriasis, it was reported that it can cause severe liver damage including cirrhosis.

Other drugs frequently prescribed are steroids, such as ACTH (a synthetic hormone) and cortisone and their derivatives. These sometimes lead to problems far worse than the original ailment; for example, steroids often lead to severe recurrences of the original conditions and adverse reactions and cortisone causes urinary losses of calcium and phosphorous, resulting in demineralization of the bones. An added problem with steroid therapy is severe depression; it invites ulcers and adrenal exhaustion with a subsequent drain on recuperative powers.

There is one known and successfully tried "drug", however, that has the approval of the FDA, but is rarely prescribed by physicians. It is the topical application of vitamin A acid. The advantages of vitamin A acid for psoriasis were first observed in double-blind controlled studies at the University of Miami School of Medicine. Doctors discovered that vitamin A in its acid form brought some relief from the itching and unsightliness of psoriasis in many patients and these effects were noticeable after a relatively short treatment (Journal of the American Medical Association, Mar. 10, 1969).

Physicians are known to have given 200,000 vitamin A units daily for six months, according to the Journal of Pediatrics (Vol. 31,496, 1947) without observing any signs of toxicity Such elevated quantities are being deemed needed, however, because vitamin A (which is already in the blood and which is stored in the liver and other body tissues) is quickly destroyed by oxygen, according to the Biochemical Journal (Vol. 34, page 1321, 1940).

BRIEF SUMMARY OF THE INVENTION

The above described disadvantages of the prior art treatments may be overcome by the hereinbelow described remedial combination of ingredients of the present invention.

It is therefore an object of the present invention to provide a treatment for psoriasis in a simple way without endangering the well being of the user through negative sides effects.

Its is still another object of the present invention to provide a combination of ingredients capable of treating psoriasis in a simple and more efficient manner by applying the lotion formed by a method and ingredients to be describe hereafter.

DESCRIPTION OF THE FORMULATION OF LOTION

The manufacturing procedure for creating the instant formulation of the lotion consists of the mixing of two pre mixed components together.

The first component referred to as Phase A is created by dissolving Methylparaben and Potassium Hydroxide into purified water which has been preheated to a temperature range between 75° and 80° Centigrade.

The second component referred to as Phase B is created by thoroughly mixing together the balance of nineteen other substances yet to be named in a separate container in any order. These nineteen ingredients are than also heated to a temperature range between 75° and 80° Centigrade.

The ingredients mixture of Phase B is than mixed into Phase A while both Phase A and Phase B are still hot and within the temperature range between 75° and 80° Centigrade.

The resultant mixture which now contains twenty two ingredients in all is allow to cool and is the instant lotion of the invention described herein.

Having described the procedure of how the instant lotion components are mixed and combined it also is necessary to illustrate the desired suitable range of proportion as follows in the below indicated table:

| Item Number & Phase | Descriptive Name | Low | Middle | High |
| --- | --- | --- | --- | --- |
| 1A | Purified Water | 83.7% | 67.4% | 34.8% |
| 2A | Methylparaben | 0.25% | 0.5% | 1.0% |
| 3A | Potassium Hydroxide | 0.4% | 0.8% | 1.6% |
| 1B | Hydrogenated Coconut Oil | 2.0% | 4.0% | 8.0% |
| 2B | Glycerine | 1.5% | 3.0% | 6.0% |
| 3B | Polysorbate 60 | 1.5% | 3.0% | 6.0% |
| 4B | Polysorbate 80 | 1.0% | 2.0% | 4.0% |
| 5B | Glyceryl Stearate (and) Laureth —23 | 1.5% | 3.0% | 6.0% |
| 6B | White Wax | 1.5% | 3.0% | 6.0% |
| 7B | Stearic Acid | 1.0% | 2.0% | 4.0% |
| 8B | Cetyl Alcohol | 0.75% | 1.5% | 3.0% |
| 9B | PEG-40 Stearate | 0.5% | 1.0% | 2.0% |
| 10B | Glyceryl Stearate | 0.3% | 0.6% | 1.2% |
| 11B | Salicylic Acid | 1.0% | 2.0% | 4.0% |
| 12B | HQ Squalane | 1.0% | 2.0% | 4.0% |
| 13B | DL-Alpha Tocopherol | 1.0% | 2.0% | 4.0% |

-continued

| Item Number & Phase | Descriptive Name | Low | Middle | High |
|---|---|---|---|---|
| | Nicotinate | | | |
| 14B | Isopropyl Myristate | 0.45% | 0.9% | 1.8% |
| 15B | EPA (Fish Oil) | 0.25% | 0.5% | 1.0% |
| 16B | Lecithin | 0.2% | 0.4% | 0.8% |
| 17B | Niacin | 0.05% | 0.1% | 0.2% |
| 18B | Vitamin B6 | 0.05% | 0.1% | 0.2% |
| 19B | Propylparaben | 0.1% | 0.2% | 0.4% |

Having thus described the procedure of how the instant lotion components are mixed and combined and the relative proportions and range of ingredients it is now appropriate to suggest the intended purpose or function that each ingredients serves in the entire mixture as a hole. The below indicated table is intended to indicate such purpose and function;

Items which have an (asterisk) * next to there name are further describe at the end of this text by manufacture supplied data sheet so as to avoid any ambiguity.

| Item Number & Phase | Descriptive Name | Purpose or Function |
|---|---|---|
| 1A | Purified Water | Inert ingredient |
| 2A | Methylparaben* | Preservative |
| 3A | Potassium Hydroxide* | Stabilizer (PH) |
| 1B | Hydrogenated Coconut Oil | Emollient |
| 2B | Glycerine* | Humectant |
| 3B | Polysorbate 60* | Emulsifier |
| 4B | Polysorbate 80* | Emulsifier |
| 5B | Glyceryl Stearate (and) Laureth −23 | Emulsifier |
| 6B | White Wax* | Thickening Agent |
| 7B | Stearic Acid* | Emulsifier |
| 8B | Cetyl Alcohol | Emulsifier |
| 9B | PEG-40 Stearate* | Thickening |
| 10B | Glyceryl Stearate | Thickening |
| 11B | Salicylic Acid | Active Ingredient |
| 12B | HQ Squalane* | Emollient Moisturizer |
| 13B | DL-Alpha Tocopherol Nicotinate* | Vitamin |
| 14B | Isopropyl Myristate* | Humectant |
| 15B | EPA | Fish Body Oils |
| 16B | Lecithin | Fat soluble phospho-lipid nutrient |
| 17B | Niacin | Vitamin |
| 18B | Vitamin B6 | Pyridovine HCL (U.S.P.) |
| 19B | Propylparaben | Preservative |

The above herein mentioned combination ingredients represent a salve or lotion thus formed, an adult may require; this may require adjustment depending upon the severity of the conditions and the weight of the person.

The recommended dosage for the relief of the symptoms of psoriasis may vary from individual to individual and its application to affected skin areas is one to four times daily or as directed by a doctor.

The foregoing is considered as illustrative only of the principles of the inventions. Further, since numerous modifications and changes will readily occur to those skilled in the art, it is not desired to limit the invention to the exact specification shown and described, and accordingly all suitable modifications and equivalents may be resorted to, falling within the scope of the invention.

What is claimed is:

1. A lotion mixture for treating psoriasis consisting of the following ingredients in the following range of proportions:
    (a) Purified Water in the range of 83.7% to 34.8%;
    (b) Methylparaben in the range of 0.25% to 1.0%;
    (c) Potassium Hydroxide in the range of 0.4% to 1.6%;
    (d) Hydrogenated Coconut Oil in the range of 2.0% to 8.0%;
    (e) Glycerine in the range of 1.5% to 6.0%;
    (f) Polysorbate 60 in the range of 1.5% to 6.0%;
    (g) Polysorbate 80 in the range of 1.0% to 4.0%;
    (h) Glyceryl Stearate (and) Laureth-23 in the range of 1.5% to 6.0%;
    (i) White Wax in the range of 1.5% to 6.0%;
    (j) Stearic Acid in the range of 1.0% to 4.0%
    (k) Cetyl Alcohol in the range of 0.75% to 3.0%;
    (l) PEG-40 Stearate in the range of 0.5% to 2.0%;
    (m) Glyceryl Stearate in the range of 0.3% to 1.2%;
    (n) Salicylic Acid in the range of 1.0% to 4.0%;
    (o) HQ Squalane in the range of 1.0% to 4.0%;
    (p) DL-Alpha Tocopherol Nicotinate in the range of 1.0% to 4.0%;
    (q) Isopropyl Myristate in the range of 0.45% to 1.8%;
    (r) EPA in the range of 0.25% to 1.0%;
    (s) Lecithin in the range of 0.2% to 0.8%;
    (t) Niacin in the range of 0.05% to 0.2%;
    (u) Vitamin B6 in the range of 0.05% to 0.2%; and
    (v) Propylparaben in the range of 0.1% to 0.4%.

2. A lotion mixture for treating psoriasis consisting of the following ingredients in the following proportions:
    (a) 67.4% Purified Water;
    (b) 0.5% Methylparaben;
    (c) 0.8% Potassium Hydroxide;
    (d) 4.0% Hydrogenated Coconut Oil;
    (e) 3.0% Glycerine;
    (f) 3.0% Polysorbate 60;
    (g) 2.0% Polysorbate 80;
    (h) 3.0% Glyceryl Stearate (and) Laureth -23;
    (i) 3.0% White Wax;
    (j) 2.0% Stearic Acid;
    (k) 1.5% Cetyl Alcohol;
    (l) 1.0% PEG-40 Stearate;
    (m) 0.6% Glyceryl Stearate;
    (n) 2.0% Salicylic Acid;
    (o) 2.0% HQ Squalane;
    (p) 2.0% DL-Alpha Tocopherol Nicotinate;
    (q) 0.9% Isopropyl Myristate;
    (r) 0.5% EPA;
    (s) 0.4% Lecithin;
    (t) 0.1% Niacin;
    (u) 0.1% Vitamin B6; and
    (v) 0.2% Propylparaben.

* * * * *